United States Patent [19]

Kolbert

[11] Patent Number: 5,223,142
[45] Date of Patent: Jun. 29, 1993

[54] PRODUCTION CHROMATOGRAPHY PROCESS USING A CRITICAL ANGLE REFRACTIVE INDEX DETECTOR

[75] Inventor: Jason H. Kolbert, Stamford, Conn.

[73] Assignee: Biotage Inc., Charlottesville, Va.

[21] Appl. No.: 932,099

[22] Filed: Aug. 18, 1992

Related U.S. Application Data

[62] Division of Ser. No. 639,870, Jan. 11, 1991, Pat. No. 5,139,661.

[51] Int. Cl.$^5$ .............................................. B01D 15/08
[52] U.S. Cl. ................................ 210/656; 73/61.58; 210/198.2; 422/70; 356/128; 356/136
[58] Field of Search ............... 210/198.2, 656; 422/70; 436/161; 73/61.52, 61.58, 61.61, 61.73; 356/128, 136

[56] References Cited

U.S. PATENT DOCUMENTS

| | | | |
|---|---|---|---|
| 2,807,976 | 10/1957 | Vossberg | 356/136 |
| 3,628,867 | 12/1971 | Brady | 356/136 |
| 3,999,856 | 12/1976 | Unterleitner | 356/361 |
| 3,999,857 | 12/1976 | David et al. | 356/133 |
| 4,952,055 | 8/1990 | Wyatt | 356/73 |

OTHER PUBLICATIONS

L. R. Snyder & J. J. Kirkland, "Introduction to Modern Liquid Chromatography", John Wiley & Sons, Inc., New York (1979) pp. 123, 129–130, 636–639.

Z. Deyl, K. Macek, & J. Janák, "Liquid Column Chromatography", Elsevier, Amsterdam (1975), pp. 146–149, 151–153.

Primary Examiner—Robert A. Dawson
Assistant Examiner—Sun Uk Kim
Attorney, Agent, or Firm—Sheldon H. Parker

[57] ABSTRACT

A critical angle refractive index detector for production liquid chromatography systems with flow rates as low as 100 ml/min to 25 l/min or higher as the system requires and pressures up to 4000 psi. The detector includes a flow cell with a sensing chamber volume selected to provide maximum detector sensitivity and minimum pressure drop at the maximum flow rate of the system for accurate discernment of critical refractive index peaks of each constituent in the sample. Explosion protected controls for zero and span settings are located to the exterior of a purged safe enclosure containing the system.

1 Claim, 2 Drawing Sheets

PRODUCTION CHROMATOGRAPHY PROCESS USING A CRITICAL ANGLE REFRACTIVE INDEX DETECTOR

This is a divisional of copending application Ser. No. 07/639,870 filed on Jan. 11, 1991, now U.S. Pat. No. 5,139,661.

BACKGROUND OF THE INVENTION

The present invention is directed to liquid chromatography and is particularly concerned with an arrangement for critical angle refractive index detectors in production chromatography systems.

In liquid chromatography a liquid sample is passed by a flowing stream of liquid solvent (the mobile phase) through a column packed with particulate matter (stationary phase). While passing through the column the various components in the sample separate from one another by adsorbing and desorbing from the stationary phase at different rates such that these individual components elute from the column at different times. The separating components then flow through a detector which responds to each component both qualitatively and quantitatively thereby providing information to the user about the constituents of the sample. The particulate matter in the chromatography column is generally referred to as the chromatography media and the resolution of the sample into its individual components by the chromatography media is a primary measure of the chromatography separation performance.

Critical angle refractive index detectors are traditionally used by heavy industries as industrially rugged monitors in large scale process pipelines. The detector is used to monitor the composition of the mixture flowing through the pipe. The traditional applications are concerned with utilizing the detector to monitor a blended stream, whose refractive index is used as a key parameter to verify the composition of the mixture being blended, e.g., syrup formulations for soda, petroleum oils, etc.

The flow rates typical in these industrial processes range between 50 to 400 liters/minute (l/min). The detector sensitivity is usually adjusted to monitor a highly specific range, e.g., a mixture whose refractive index is 1.003, will have a range set of 1.000 to 1.006. The range controls are usually internally set and adjusted only for calibrations. In contrast, chromatography applications would call for flow rates as low as 100 ml/min, and ranges of detection which change on a daily basis or even more frequently. Range controls for zero and sensitivity (span) would need to be readily accessible to the end user. The goal of the chromatography application is not to monitor a blended stream for consistent composition but to detect compounds which have been separated and purified as they elute the chromatography column. The chromatographer is not concerned with the true or real value of the refractive index of the mobile phase and eluting peaks; the concerns are in distinguishing the presence of eluted peaks in the mobile phase as they occur, i.e., the detector's response to the temporary presence of eluting compounds.

The critical angle detector utilizes the principles of refractive index in combination with a prism, to measure light returned as a function of the critical angle which, in turn, is a function of the refractive index of a liquid flowing past the prism. The only surface in contact with the liquid is that of the solid prism. An LED light source emits light through the prism, some of which is lost into the liquid, while the remaining amount is refracted and returns through the prism and is measured by a photodiode generating a signal whose response is proportional to the liquid's refractive index properties at the prism surface. The result is a rugged detector which can withstand high flow rates and large back-pressures (as high as 4000 psi).

Traditional refractive index detectors used in chromatography are known as differential refractive index detectors. The flow cell is usually constructed of delicate glued sections of quartz, resulting in a fragile cell. The cell is comparted with a sample side and reference side. Maximum flow and pressure rating tend to be in the 100 ml/min, 100 psi range. The detector, however, can be made quite sensitive to minute concentrations of sample, which in analytical chromatography is a key criterion. In preparative applications, such high sensitivity is not required. In the past, preparative chromatography equipment would use differential refractive index detectors and would, due to flow rate limitations of the flow cell, split a small sample stream through the detector's flow cell ("split stream detection"). The approach has been cumbersome with maintenance problems and performance issues as to whether the split stream sample is truly representative of the main stream composition.

SUMMARY OF THE INVENTION

There is a need for a more appropriate industrially rugged refractive index detector that is of value and functional for preparative chromatography applications.

According to the present invention a process solution is directed through a full flow-through cell which has been optimized for a maximum sensitivity by minimizing extraneous mixing between the eluting components and the carrier stream (the mobile phase) a phenomenon known as "band spreading". A second consideration of a proper flow cell design is to minimize the amount of pressure drop created as the fluid moves through the cell. An acceptable pressure drop is characterized as between 1-2% of the system's pressure rating. The essence of the flow cell design is to provide a sensing chamber where detection can occur without interrupting or disturbing the pattern of the fluid which is flowing through the process. Specifically these considerations are achieved by designing a flow cell with an internal volume related to pipe diameter and experimental parameters for maximizing detector sensitivity and minimizing pressure drop through the flow cell at maximum flow rate.

The design of the flow cell may be optimized in production chromatography systems for capacities as large as the process requires, 25.0 l/min and higher, or as low as 100 ml/min. Pressure ranges as high as 4000 psi have been achieved with the current design as well.

A second aspect of the invention involves the design of the controls for zero and for span. It was determined that the useful aspects of critical angle refractive index detection in production chromatography applications would require controls that were readily accessible to the operator and such that could be located remotely from the principal detector circuitry in the hazardous environment as defined in the National Electric Code for Class 1, Division I Groups C & D environments where large volumes of explosive chemicals are used. This is accomplished by selecting "explosion proof"

rated potentiometers for these hazardous environments. These are mounted on the exterior of a purged "safe" enclosure. These controls provide the operator with the capability to easily set and reset the (baseline) refractive index of the mobile phase to zero, to set the refractive index range (sensitivity) as required by the particular chromatography operation. The net result is a useful critical angle refractive index detector suitable for production chromatography applications.

The principle of operation of the critical angle refractive index detector is as follows. The process fluid is in contact with a sapphire window where the detection occurs. A light emitting diode (LED) light source is focused on the window by use of collimating and focusing lenses. The light then passes through the sapphire window and is reflected to the interface boundary where the wetted surface of the window is exposed to the process fluid. The light striking the interface boundary is either reflected back through the sapphire window or lost into the process fluid. The amount of light returning is a function of the refractive index of the process fluid and is measured by a light sensitive silicon wafer.

In this way the chromatographer is able to distinguish the presence of eluted peaks in the mobile phase as they occur.

The invention provides a robust device suitable for the industrially rugged environment of large scale process chromatography.

OBJECTS OF THE INVENTION

It is an object of the invention to provide a critical angle refractive index detector useful in preparative and process scale chromatography.

Another object of the invention is to provide a critical angle refractive index detector for chromatography which monitors the full flow of process fluid, avoiding the necessity of using a split stream.

Another object of the invention is to provide a critical angle refractive index detector which minimizes extraneous mixing between the eluting components and the carrier stream.

Another object of the invention is to provide a critical angle refractive index detector having a flow cell design minimizing pressure drop of fluid moving through the cell.

Another object of the invention is to provide critical angle refraction index detector capable of handling flows of up to 25.0 l/min and higher and system pressures of up to 4000 psi.

Another object of the invention is to provide a critical angle refractive index detector which is safe for chromatography operations in a hazardous environment.

Other and further objects of the invention will occur to those skilled in the art upon employment of the invention in practice and upon an understanding of the following detailed description.

DESCRIPTION OF THE DRAWING

A preferred embodiment of the invention has been chosen for purposes of describing and illustrating the principles of the invention and is shown in the accompanying drawing in which.

DETAILED DESCRIPTION OF THE INVENTION

Figure 1:
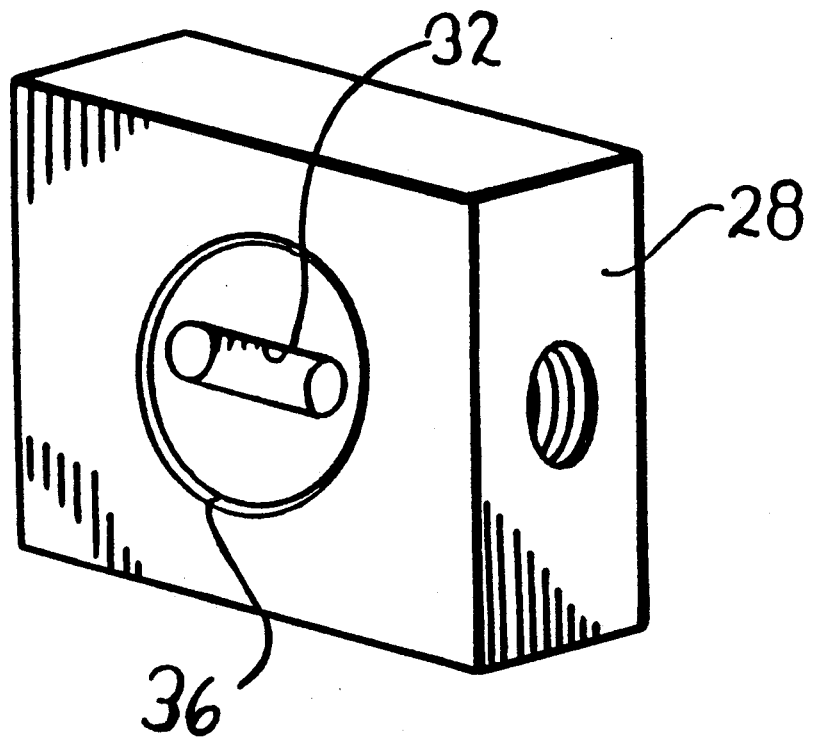
FIG. 1 is an exploded schematic view of a refractive index detector for liquid chromatography according to the present invention.

Referring now to the drawing, the present invention is applied to the full flow path of a liquid chromatography system in which a liquid sample 10 under scrutiny passes through a flow line 12 having an inspection window 14 through which the critical angle refractive index detector determines a refractive index response concerning the solution flowing through the system.

As shown in the drawing a light source 16 from a light emitting diode, is directed through a collimating lens 18 and through a focusing lens 20 and directed into a sapphire window (prism) 14 positioned over the process fluid 10. The emitted light strikes the window at an angle of incidence suitable for the material to be detected and is thereafter reflected and refracted with the reflected light being directed by the sapphire window which acting like a prism directs the returning light to a detector in the form of a silicon wafer 22.

The angle at which the cone of infra red light enters the sensing window is chosen to encompass the "critical angle" which is the specific angle of incidence where the light rays traveling through the sapphire sensing window either break through the interface (wetted surface) or reflect from the interface surface as if it were a mirror. All of the light rays above the critical angle pass through the wetted interface 24 and are lost in the liquid stream. Light rays below the critical angle reflect from the wetted surface at the same angle of incidence. The critical angle is a function of the refractive index of the sapphire window and of the material being examined, the process fluid.

Figure 2:
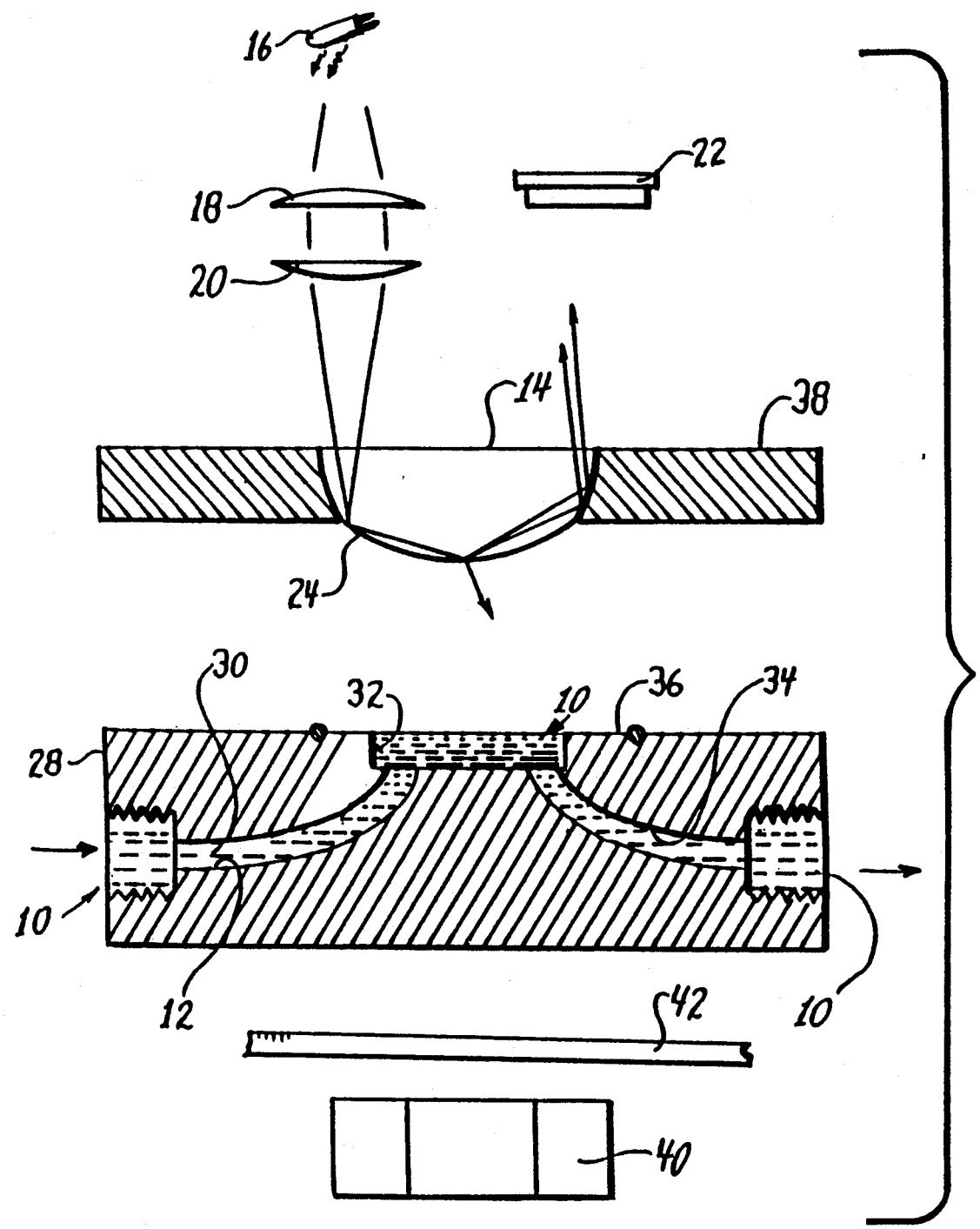
FIG. 2 is a perspective view of the detection chamber of the flow cell.

The detector of FIG. 1 includes a two-piece flow cell housing 26 of stainless steel construction for passing the entire fluid flow of the system through the flow cell. The lower portion 28 of the housing includes an internal passage 12 including an inlet duct 30, a detection chamber 32 and an outlet passage 34. An o-ring seal 36 surrounds the detection chamber. The upper portion is a cap member 38 for positioning the prism 14 in operative relation enclosing the detection chamber 32. Design considerations include evaluating the internal volume of the cell for optimum sensitivity as well as the overall design considerations of the internal flow path 12, 30, and 34 to minimize pressure drop through the cell. As shown in FIG. 2, the detection chamber is tubular in form having a predetermined overall length l and diameter d.

The flow cell 28, 38 has been optimized to provide maximum sensitivity, refractive index response by controlling the internal volume of detection chamber 32 in contact with the sensing window 14.

Flow cell internal volume is determined as follows:

$$Vol_{cell} = \pi/4 \, d^2 l)$$

where
- d is diameter of the tubular detection chamber of the flow cell, and
- l is the length of the detection chamber and is in a range of 1–4 cm determined experimentally to (a) maximize detector sensitivity and (b) to minimize pressure drop through the flow cell at maximum flow rate.

In applying the critical angle refractive index detector to production chromatography, explosion protected potentiometers 40 must be used for setting and resetting the (baseline) refractive index of the mobile phase to zero and to the refractive index range as required by a particular chromatography operation. These controls are mounted to the exterior of a purged safe enclosure 42.

In a test performed utilizing a critical angle refractive index detector, the following conditions prevailed. The liquid sample flow rate was 200 ml/min. The mobile phase was 20% ethyl acetate in methylene chloride. The chromatography column measured 5 centimeters by 50 centimeters long and was packed with 400 grams of silica gel having 40 to 60 micron particle size. The test sample was 20 grams of a 50/50 mixture of steroids the first being 4-androstene-3,17-dione and the second being 1,4 androstene-3,17-dione. During the chromatography test run, the eluent from the column was monitored utilizing the critical angle refractive index detector. The eluent was monitored for two responses, peak A and peak B, the two steroids separated from the compound test mixture. The detector's response was analyzed for appropriate sensitivity such that the compounds could be clearly visualized from the background response and after review was found to be adequate and useful.

I claim:

1. In a production chromatography process wherein the constituents in fluid eluted from a chromatography column are to be identified in the detector chamber of a critical angle refractive index detector the steps comprising establishing the volume of said detector chamber in accordance with the formula $v = \pi/4 \, d^2 l$ where d is the diameter of the inlet to the detector chamber and l is the length of the chamber in the range of 1 to 4 centimeters which dimension is experimentally determined to provide maximum detector sensitivity and a minimal pressure drop of 1 to 2% of the system pressure at maximum flow rate through the detector chamber, passing the full flow of elutant of from 100 ml/min to 1 /min or more from said chromatography column through said detector chamber of said critical angle refractive index detector at pressures up to 4000 psi and identifying constituents in said detector chamber by means of said critical angle refractive index detector which registers the presence of particular constituents in the mobile phase as eluted peaks.

* * * * *